United States Patent
Stark

(10) Patent No.: US 6,255,656 B1
(45) Date of Patent: Jul. 3, 2001

(54) POSITIONER FOR A SCINTILLATION CAMERA DETECTOR HEAD

(75) Inventor: Iain Stark, Nepean (CA)

(73) Assignee: IS² Research Inc. (CA)

( * ) Notice: Subject to any disclaimer, the term of this patent is extended or adjusted under 35 U.S.C. 154(b) by 0 days.

(21) Appl. No.: 09/127,982

(22) Filed: Aug. 3, 1998

(30) Foreign Application Priority Data

Aug. 1, 1997 (CA) .................................................. 2212196

(51) Int. Cl.⁷ .................................................. G01T 1/166
(52) U.S. Cl. .............................. 250/363.08; 250/363.01; 250/363.06
(58) Field of Search ........................ 250/363.08, 363.01, 250/363.03, 363.06

(56) References Cited

U.S. PATENT DOCUMENTS

| | | |
|---|---|---|
| 3,765,549 | 10/1973 | Jones . |
| 4,064,441 | 12/1977 | Casale . |
| 4,216,381 | 8/1980 | Lange . |
| 4,223,222 | 9/1980 | Gray et al. . |
| 4,426,578 * | 1/1984 | Bradcovich et al. ............ 250/363.08 |
| 4,578,585 * | 3/1986 | Gosis et al. ..................... 250/363.08 |
| 4,590,378 * | 5/1986 | Platz ................................ 250/363.08 |
| 4,651,007 | 3/1987 | Perusek et al. . |
| 4,774,411 * | 9/1988 | Span ................................ 250/363.08 |
| 5,047,641 | 9/1991 | Besseling et al. . |
| 5,146,094 | 9/1992 | Stark . |
| 5,262,648 | 11/1993 | Stark . |
| 5,523,571 * | 6/1996 | Velazquez et al. ............. 250/363.08 |

* cited by examiner

Primary Examiner—Constantine Hannaher
Assistant Examiner—Otilia Gabor
(74) Attorney, Agent, or Firm—Finnegan, Henderson, Farabow, Garrett & Dunner, L.L.P.

(57) ABSTRACT

A positioner for a scintillation camera detector head is designed for use with a detector head of the type having a center of gravity dependent upon the weight of a removable collimator plate and being supported between a pair of substantially parallel support arms such that the detector head is rotatable relative to the support arms about an axis of rotation passing through the support arms. The positioner includes a pair of rigid detector head links for aligning the center of gravity of the detector head relative to the support arms. Each detector head link includes an arm end rotatably attached to the adjacent support arm by way of an arm axle, and a head end rotatably attached to the detector head by way of a head axle. The positioner also includes a lock for selectively securing the relative positions of the detector head and the detector head links.

7 Claims, 11 Drawing Sheets

POSITIONER FOR A SCINTILLATION CAMERA DETECTOR HEAD

FIELD OF INVENTION

The present invention relates to a centre of rotation adjustor for a scintillation camera detector head.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

The detector head of a scintillation camera includes a casing in which is contained the scintillator crystal and the photomultiplier tubes. Attached to the underside of the casing is a collimator or collimator plate, which is a sheet of absorbing material, usually lead, perforated by relatively narrow channels.

A particular design and weight of collimator must be selected depending on the isotope being used or the type of study being conducted. Thus, the collimator plate attached to the detector head must be changed from time to time. Collimator plates vary considerably in weight.

Generally, a detector head is supported by a pair of support arms. Since the angle of the detector head relative to the patient must be selectable, the detector head must be rotatable relative to the arms.

If a detector head is rotatable relative to the support arms at a point close to the centre of gravity of the detector head, then the angle of the detector head relative to a patient may be adjustable by hand. However, changing the collimator plates moves the centre of gravity of the detector head. Since collimator heads are so heavy, it becomes inconvenient or impossible to adjust the angle of the detector head by hand.

One prior art solution to the problem of adjusting the angle of a detector head is to provide an electric motor to adjust the angle of the detector head relative to the arms. However, the use of electric motors adds to the cost of manufacturing the machine. Furthermore, it is generally faster and more convenient to adjust the angle of the detector head by hand.

Another prior art solution is to adjust the point of rotation of the detector head relative to the support arms by providing lead screws driven by an electric motor. Again, the use of electric motors adds to the cost of manufacturing the machine. Furthermore, adjusting the point of rotation of the detector head using lead screws is time consuming.

SUMMARY OF THE INVENTION

An object of the invention is to provide an improved centre of rotation adjustor for a scintillation camera detector head.

A second object of the invention is to provide a centre of rotation adjustor for a scintillation camera detector head that is convenient to use.

A third object of the invention is to provide a centre of rotation adjustor for a scintillation camera detector head that avoids to use of a motor.

The invention relates to a positioner for a scintillation camera detector head. The detector head is of the type having a centre of gravity dependent upon the weight of a removable collimator plate and being supported by at least one support arm such that the detector head is rotatable relative to the support arm about an axis of rotation passing through the support arm. The positioner of the present invention includes a rigid detector head link for aligning the centre of gravity of the detector head relative to the support arm. The detector head link includes an arm end rotatably attached to the support arm. The detector head link also includes a head end rotatably attached to the detector head. The positioner also includes a lock for selectively securing the relative positions of the detector head and the detector head link.

An embodiment of the invention relates to a positioner for a scintillation camera detector head. The detector head is of the type having a centre of gravity dependent upon the weight of a removable collimator plate and being supported between a pair of substantially parallel support arms such that the detector head is rotatable relative to the support arms about an axis of rotation passing through the support arms. The positioner includes a pair of rigid elongate detector head links for aligning the centre of gravity of the detector head relative to the support arms. Each detector head link is substantially parallel to an adjacent support arm. Each detector head link includes an arm end rotatably attached to the adjacent support arm by way of an arm axle. Each detector head link also includes a head end rotatably attached to the detector head by way of a head axle. The positioner also includes a pair of locks for selectively preventing rotation of the detector head relative to the detector head links. Each lock includes a collimator support extending from the detector head adjacent the collimator plate. Each lock also includes a block for supporting the detector head link on the collimator support. Each block includes a pair of pins located either side of the head axle.

According to the invention, there is provided a positioner for a scintillation camera detector head, the detector head having a centre of gravity dependent upon the weight of a removable collimator plate and being supported by at least one support arm such that the detector head is rotatable relative to the support arm about an axis of rotation passing through the support arm, the positioner comprising: a rigid detector head link for aligning the centre of gravity of the detector head relative to the support arm, the detector head link comprising: an arm end rotatably attached to the support arm; and a head end rotatably attached to the detector head; and a lock for selectively securing the relative positions of the detector head and the detector head link.

According to the invention, there is further provided a positioner for a scintillation camera detector head, the detector head having a centre of gravity dependent upon the weight of a removable collimator plate and being supported between a pair of substantially parallel support arms such that the detector head is rotatable relative to the support arms about an axis of rotation passing through the support arms, the positioner comprising: a pair of rigid elongate detector head links for aligning the centre of gravity of the detector head relative to the support arms, each detector head link being substantially parallel to an adjacent support arm and comprising; an arm end rotatably attached to the adjacent support arm by way of an arm axle; and a head end rotatably attached to the detector head by way of a head axle; and a pair of locks for selectively preventing rotation of the detector head relative to the detector head links, each lock comprising: a collimator support extending from the detector head adjacent the collimator plate; and a block for supporting the detector head link on the collimator support, each block comprising a pair of pins located either side of the head axle.

Advantageously, the present invention provides: an improved centre of rotation adjustor for a scintillation camera detector head; a centre of rotation adjustor for a scintillation camera detector head that is convenient to use; and a centre of rotation adjustor for a scintillation camera detector head that avoids to use of a motor.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

Figure 1:
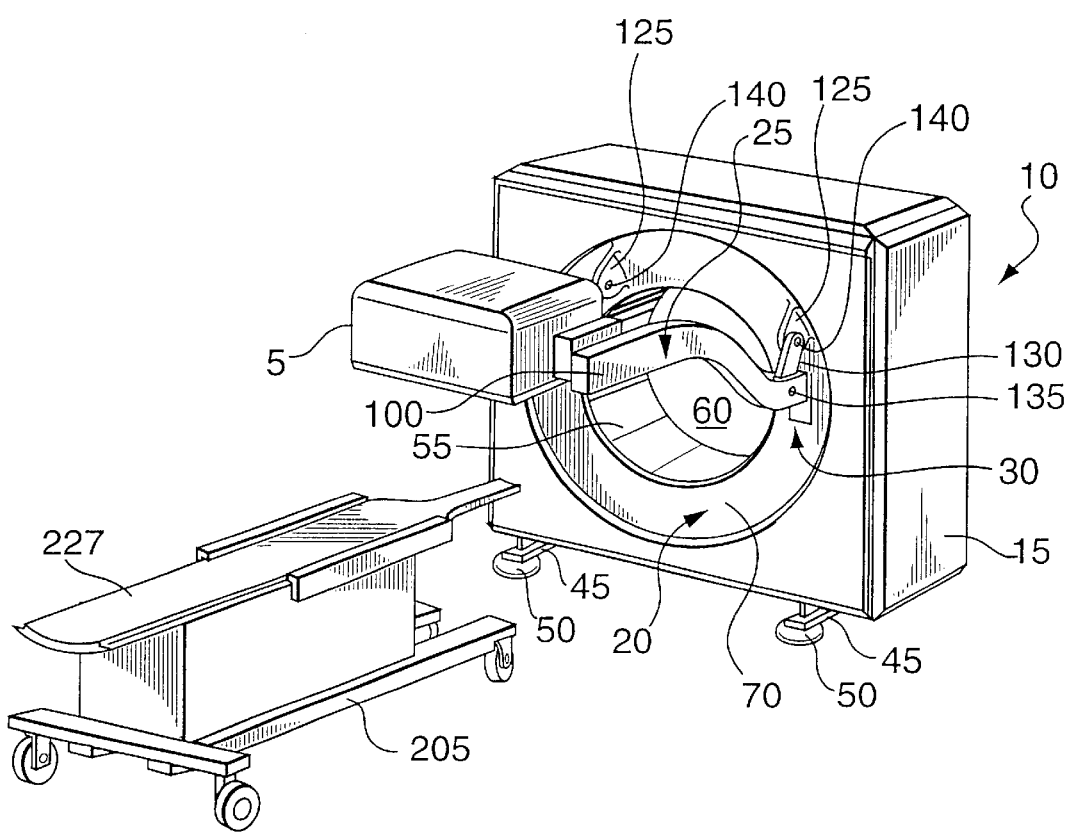
FIG. 1 is a perspective view of a scintillation camera including a detached patient support in accordance with the invention.
Figure 2:
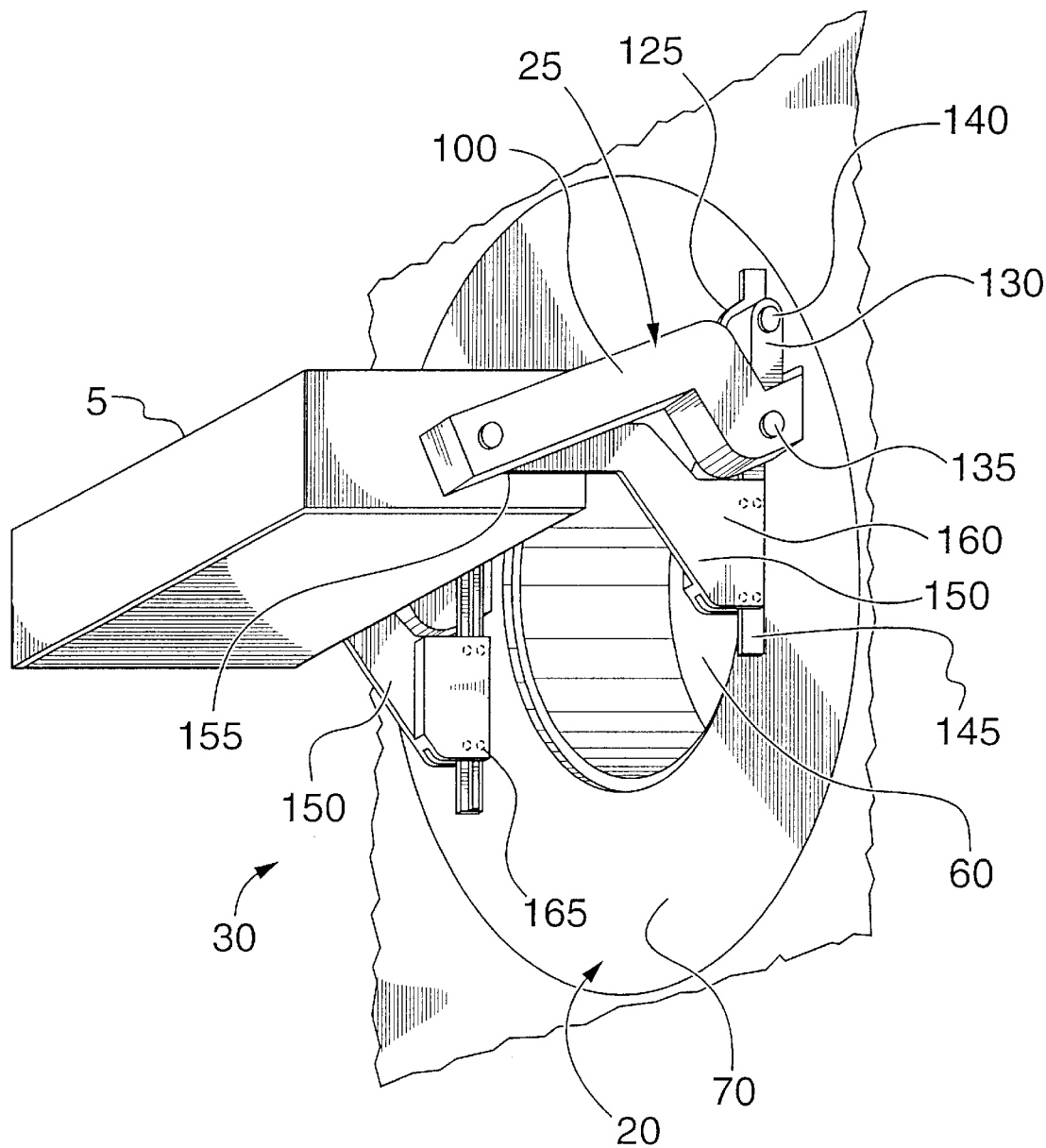
FIG. 2 is a perspective view of the guide of a scintillation camera.
Figure 3:
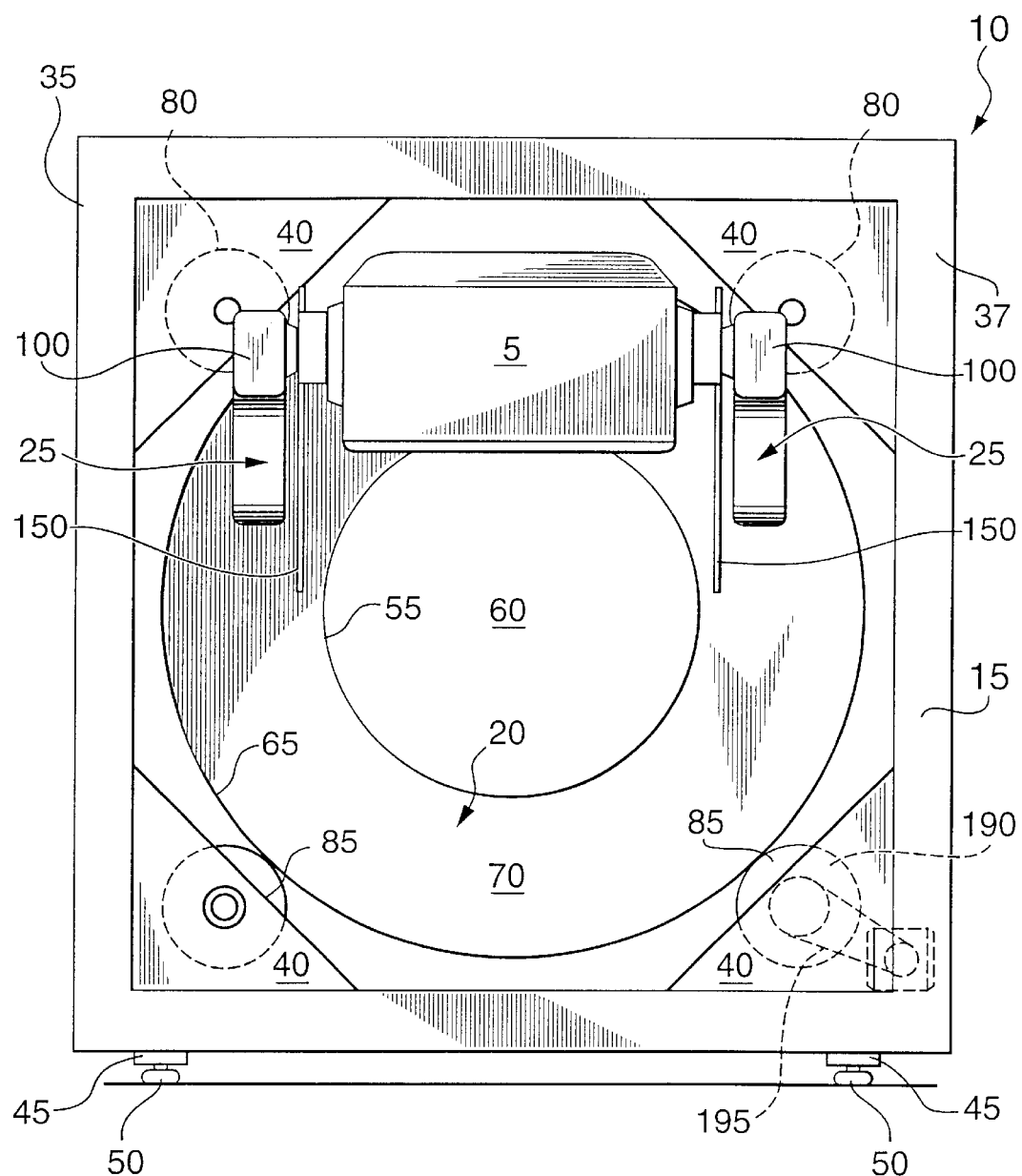
FIG. 3 is a front elevation view of a scintillation camera.
Figure 4:
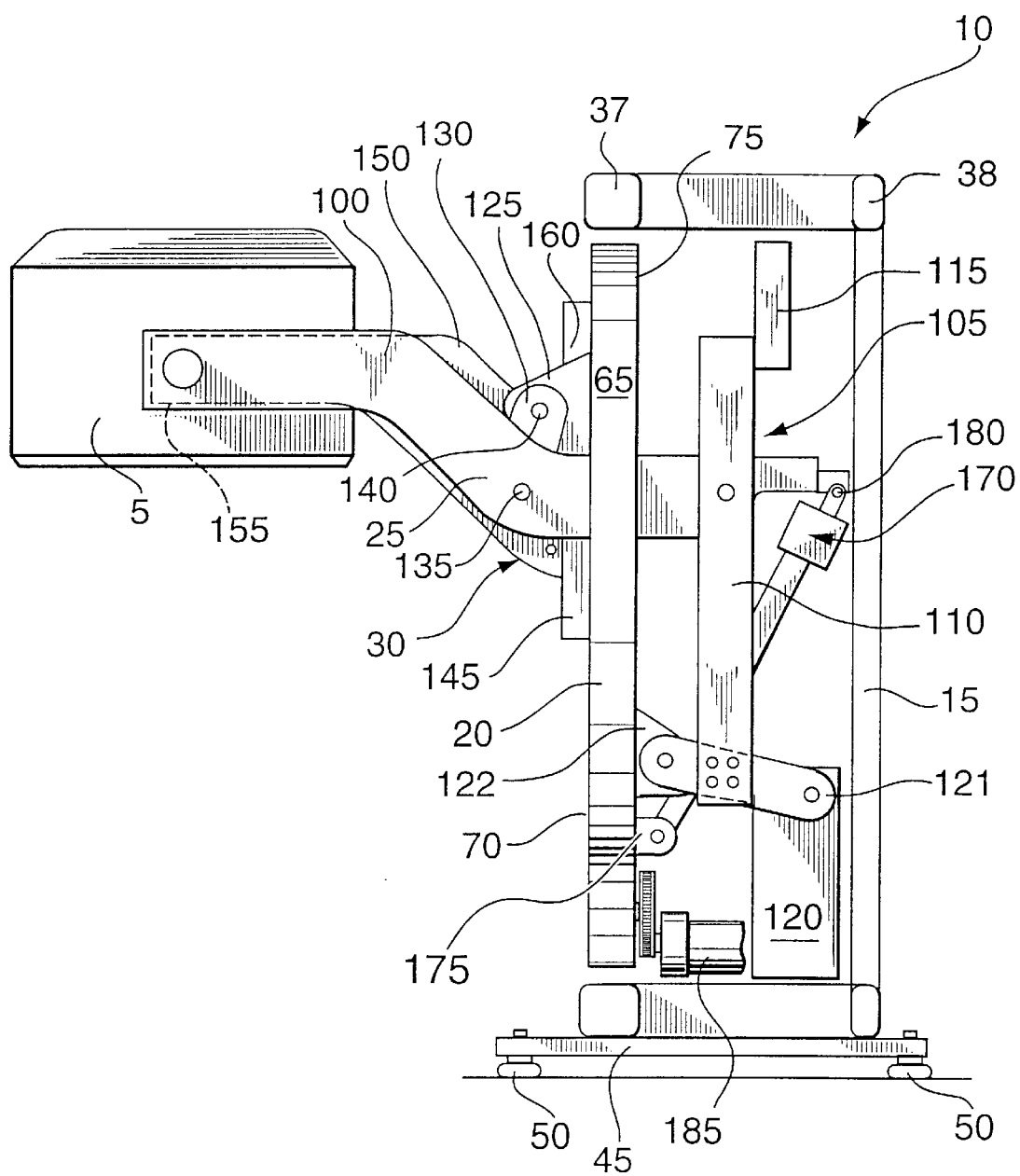
FIG. 4 is a side elevation view of a scintillation camera.
Figure 5:
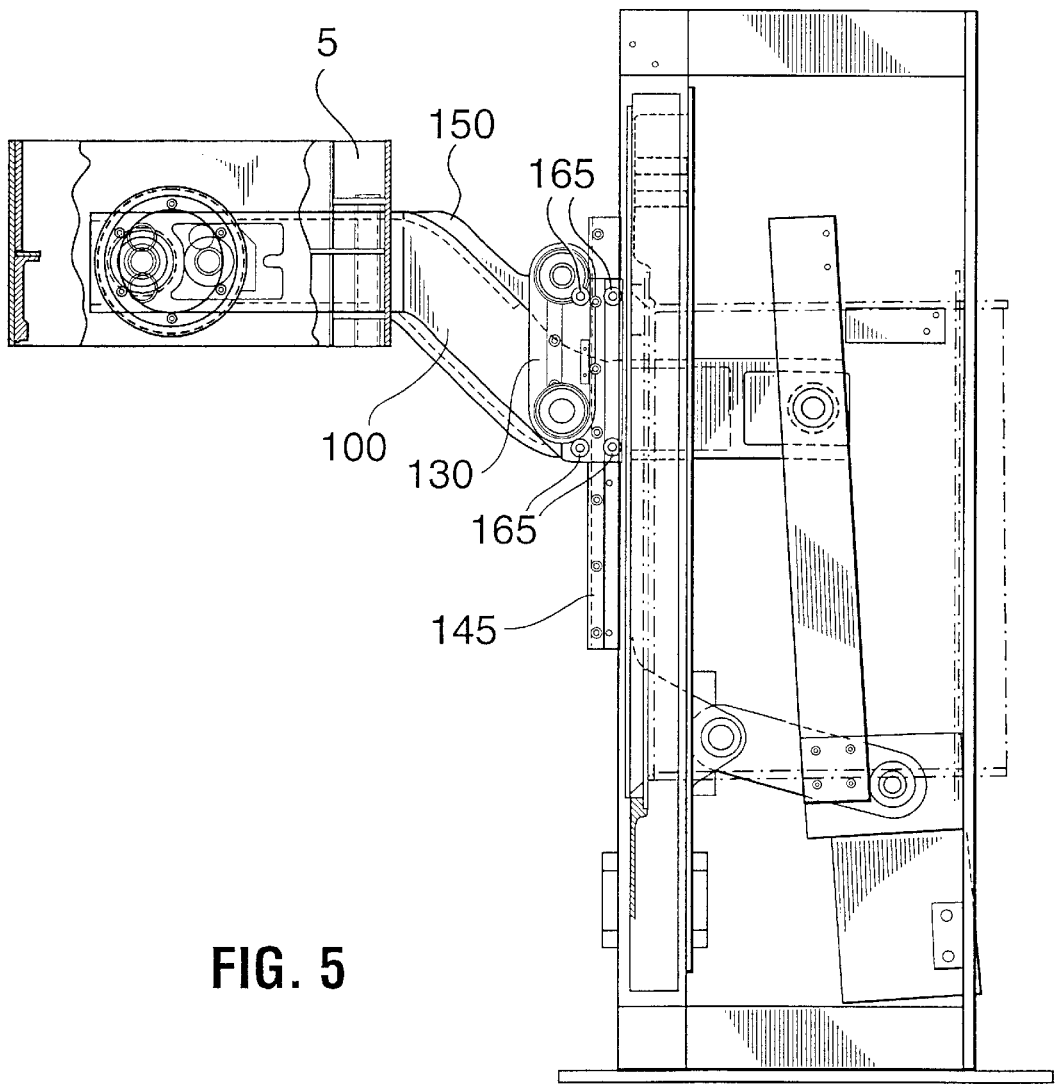
FIG. 5 is a side elevation view of a scintillation camera.
Figure 6:
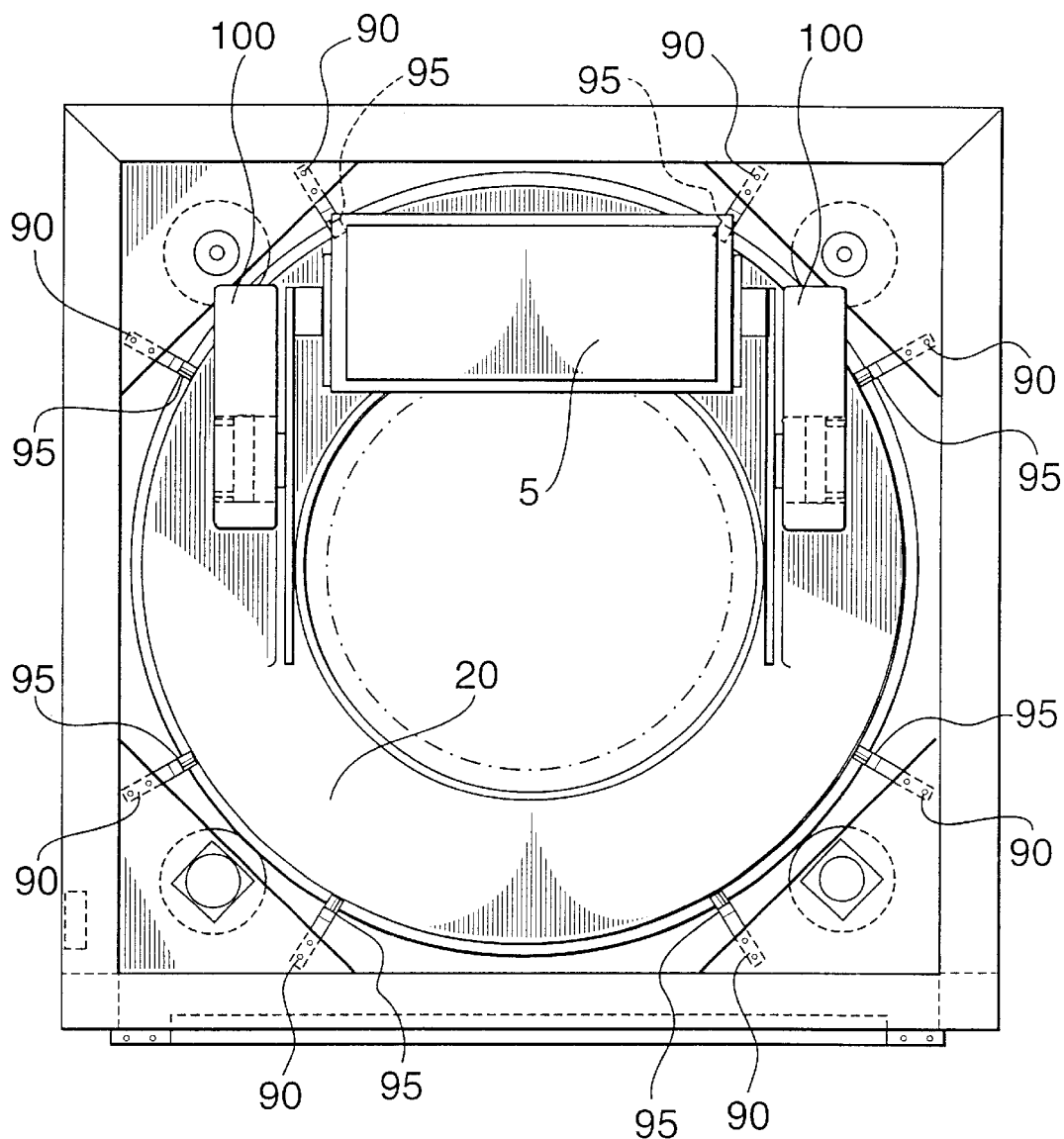
FIG. 6 is a front elevation view of a scintillation camera.
Figure 7:
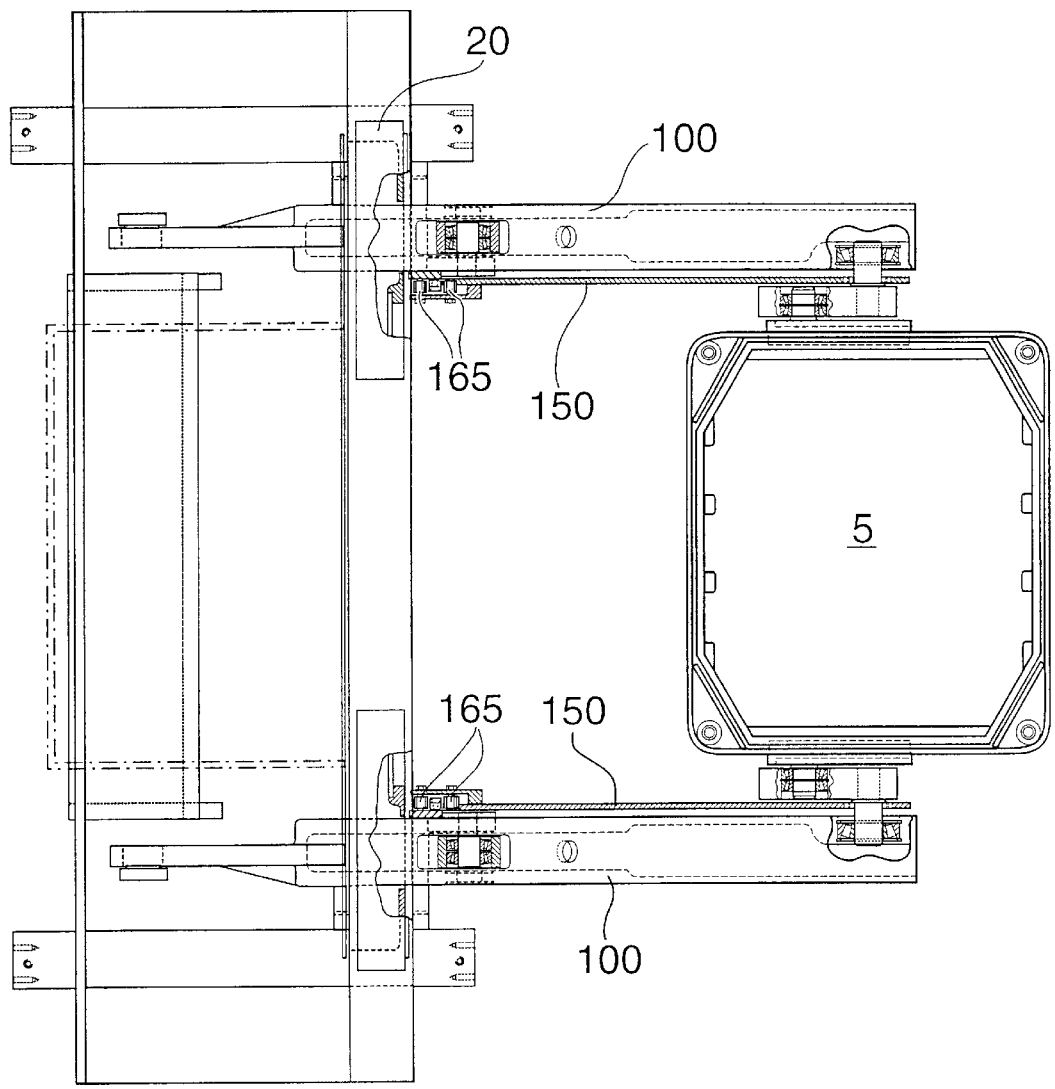
FIG. 7 is a top plan view of a scintillation camera.
Figure 8:
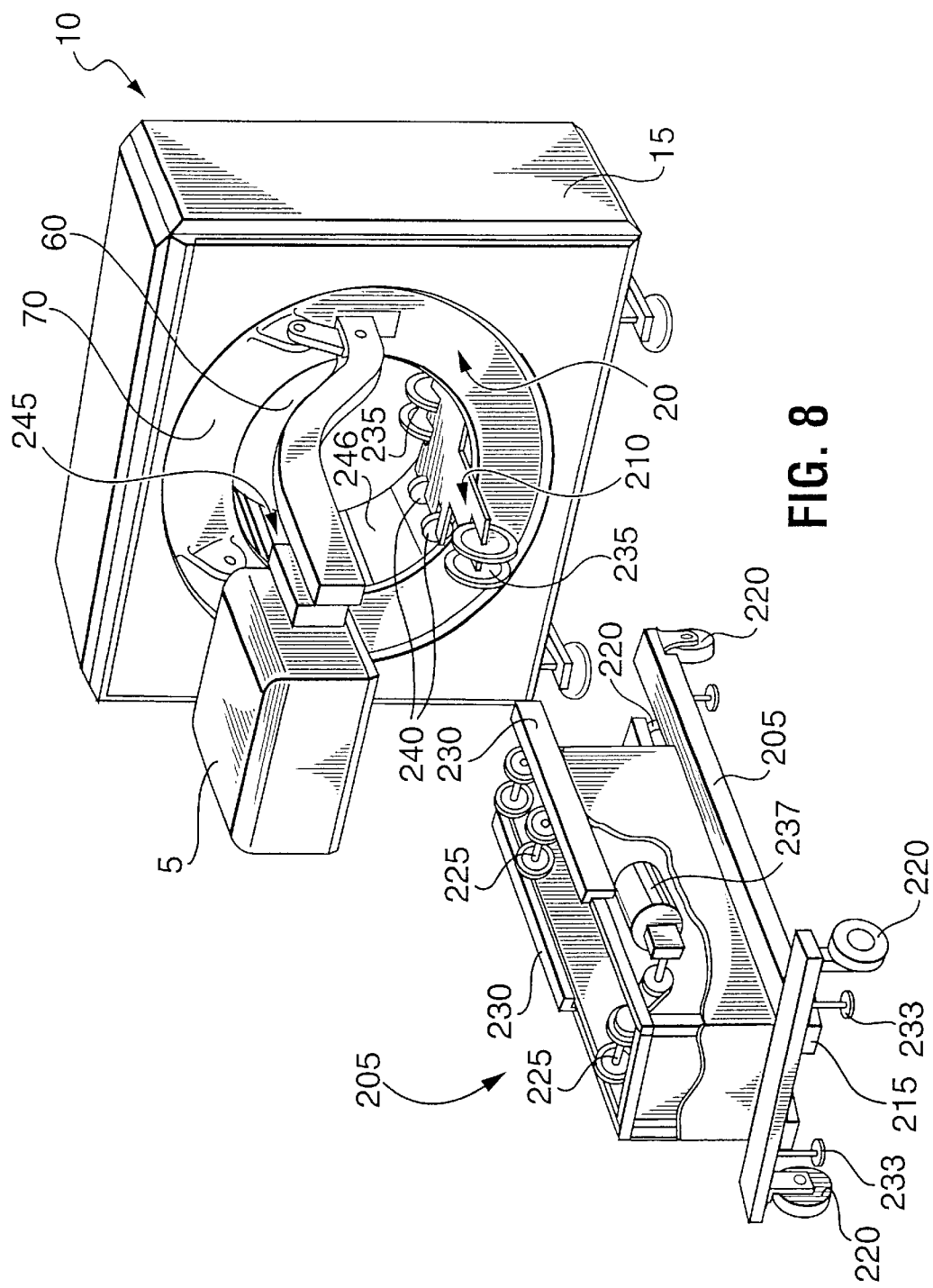
FIG. 8 is a perspective view of the scintillation camera of FIG. 1, including the detached patient support and engaged patient support, with the stretcher removed.
Figure 9:
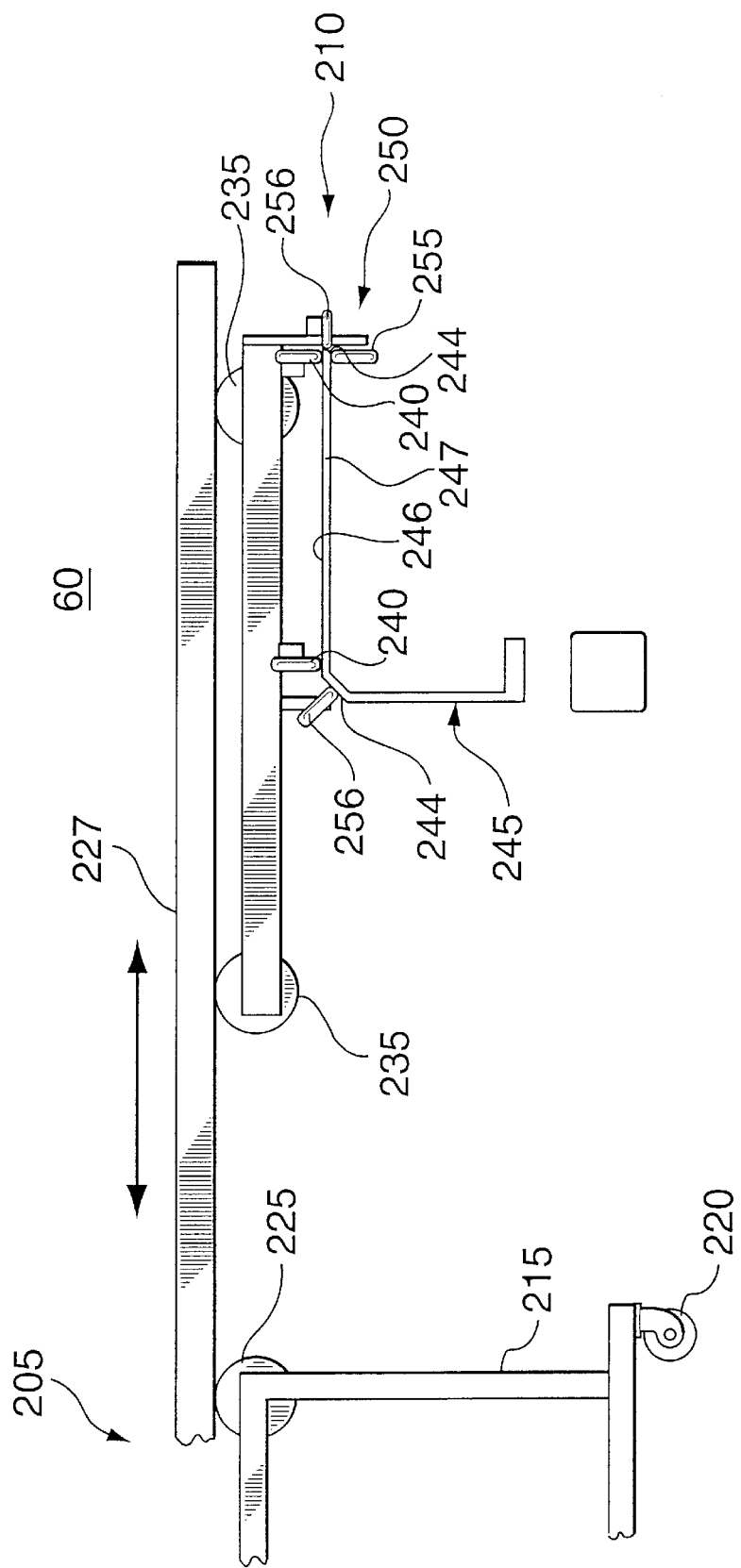
FIG. 9 is a side view of a portion of the patient support apparatus.

Similar references are used in different figures to denote similar components.

DETAILED DESCRIPTION OF THE INVENTION

Referring to FIGS. 1 to 12, a nuclear camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep. The frame 35 also includes eight triangular corner braces 40 welded to the front square section 37, that is, each corner of the front square section 37 has two corner braces 40, one towards the front of the front square section 37, and one towards the rear of the front square section 37. In the illustrated embodiment, the corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches (about 132 centimeters). The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20. Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 65 is adjustable. The curved surfaces of the upper rollers 80 and lower rollers 85 (i.e. the surfaces that contact the outer surface 65) should be tough so as to be able to withstand the pressures exerted by the annular support 20, and should have a fairly high coefficient of friction so as to roll consistently relative to the annular support 20.

Attached to each pair of corner braces 40 is a stabilizing arm (not shown) oriented perpendicularly to the plane of the annular support 20. A pair of small stabilizing rollers are mounted (not shown) onto each stabilizing arm. Each pair of stabilizing rollers is positioned such that one stabilizing roller rolls on the front surface 70, and the other stabilizing roller rolls on the rear surface 75. The stabilizing rollers maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205, an engaged patient support 210, and a cylinder 245.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 245 is rigidly mounted to the annular support 20. The cylinder 245 is aligned with the orifice 60 of the annular support 20 such that the cylinder is coaxial with the annular support 20. The cylinder 245 includes a smooth inner surface 246 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 250. The stabilizer 250 includes outside wheels 255 to maintain the engaged patient support 210 horizontal, that is, to stop the engaged patient support from tipping relative to the cylinder 245. The outside wheels 255 roll on the outside surface 243 of the cylinder 250. The stabilizer 245 also includes end wheels 256 to prevent the engaged patient support 210 from moving in a direction parallel to the axis of the cylinder 215. The end wheels 256 roll on the ends 244 of the cylinder 245.

Figure 10:
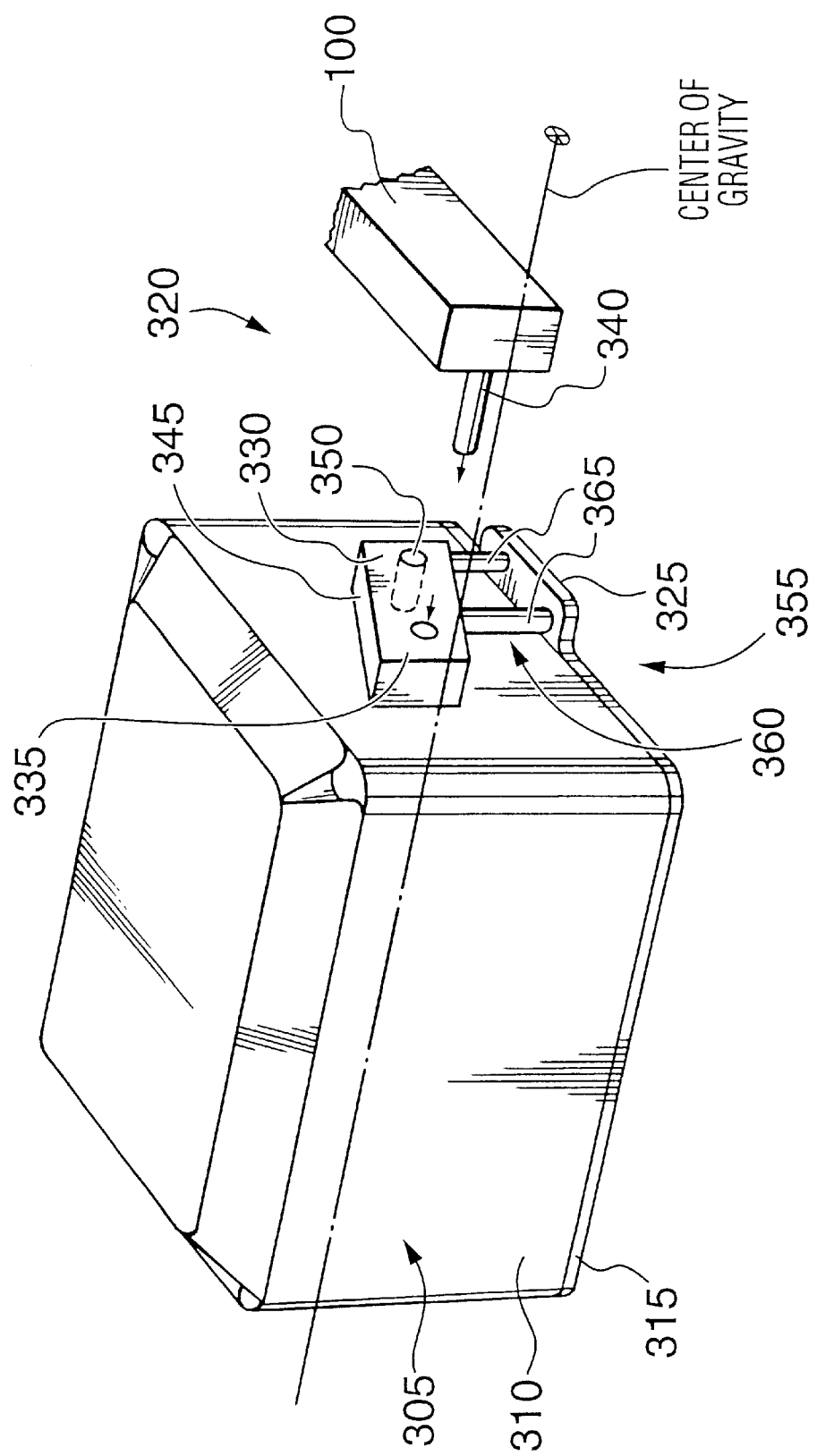
FIG. 10 is a perspective view of the positioner of the present invention.
Figure 11:
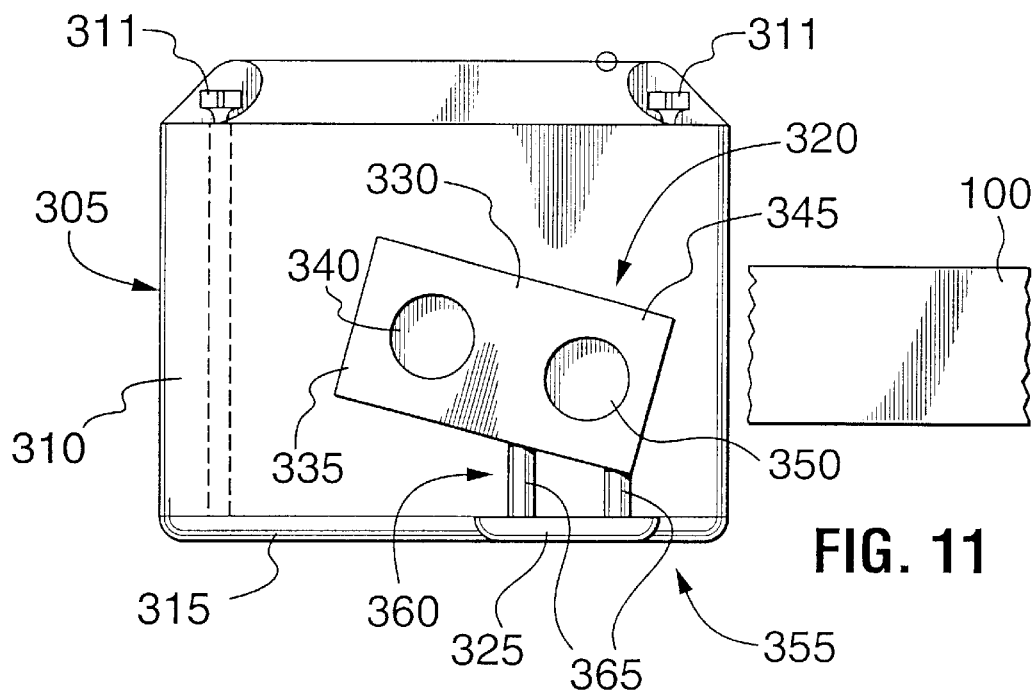
FIG. 11 is a side elevation view of the positioner of the present invention.
Figure 12:
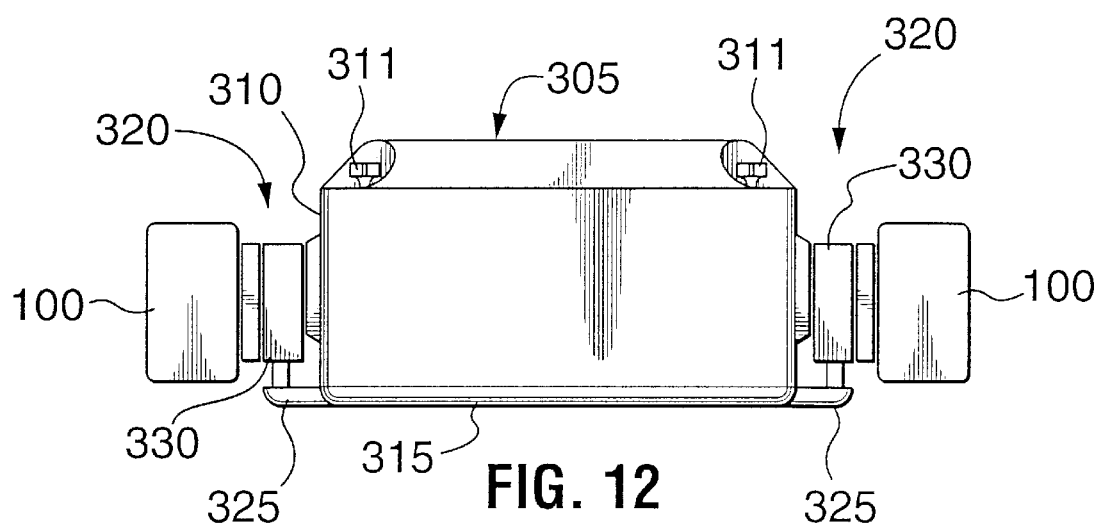
FIG. 12 is a front elevation view of the positioner of the present invention.

FIGS. 10, 11 and 12 illustrate a preferred embodiment of the present invention. A detector head 305 of the nuclear camera 5 is supported between the two support arms 100 by a positioner 320. The detector head 305 includes a casing 310 in which is contained a scintillation crystal and photomultiplier tubes. Attached to the underside of the casing 310 is a collimator plate 315. The collimator plate 315 is made of lead perforated by narrow channels, and includes a collimator support 325 extending from the two edges of the collimator plate adjacent the support arms 100. The collimator plate 315 is attached to the casing 310 by way of bolts 311. By removing the bolts 311, the collimator plate 315 can be removed from the casing 310 and replaced by another collimator plate 315. A particular design and weight of collimator is selected depending on the isotope being used or the type of study being conducted. Thus, the collimator plate 315 must be changed from time to time. Since the collimator plates 315 vary considerably in weight from one to another, the location of centre of gravity of the detector head 305 is dependent upon the weight of the collimator plate 315 attached to the casing 310. Since the angle of the detector head 305 relative to the patient must be adjusted by an operator of the nuclear camera 5, the detector head 305 must be rotatable relative to the arms 100. If the centre of gravity of the detector head 305 is positioned approximately on the axis of rotation of the detector head relative to the support arms 100, then the detector head 305 will be balanced, and the angle of the detector head 305 relative to the support arms 100 will be adjustable by hand. However, changing the collimator plates moves the centre of gravity of the detector head. Since collimator plates 315 are so heavy, it becomes inconvenient or impossible to adjust the angle of the detector head 305 by hand. The positioner 320 enables the operator to adjust the position of the centre of gravity of the detector head 305 to be approximately aligned with the point of rotation of the detector head 305, which passes through the support arms 100.

The positioner 320 attaches the detector head 305 to the support arms 100 and includes a pair of rigid elongate detector head links 330 for aligning the centre of gravity of the detector head 305 relative to the support arms 100. Each detector head link 330 is rotatable relative to the support arms 100 in a plane substantially parallel to its adjacent support arm 100. Each detector head link 330 includes an arm end 335 rotatably attached to the adjacent support arm 100 by way of an arm axle 340. Each detector head link 330 also includes a head end 345 rotatably attached to the detector head 305 by way of a head axle 350.

The positioner 320 also includes a pair of locks 355 for selectively preventing rotation of the detector head 305 relative to the detector head links 330. Each lock 355 includes the collimator support 325 extending 305 from the collimator plate 315. Each lock 355 also includes a block 360 for supporting the detector head link 330 on the collimator support 325. Each block 360 includes a pair of pins 365 located either side of the head axle 350.

In operation, each lock 355 supports the head end 345 of one of the detector head links 330 on the corresponding collimator support 325. Thus, the distance between the head axle 350 and the collimator support 325 remains constant, and rotation of the detector head 305 relative to the detector head link 330 is prevented.

If a heavier collimator plate 315 is installed, shorter pins 365 are installed, thus reducing the distance between the head axle 350 and the collimator support 325, and aligning the centre of gravity of the detector head 305 with the axis of rotation of the detector head 305, which passes through the arm axles 340.

If a lighter collimator plate 315 is installed, longer pins 365 are installed, thus increasing the distance between the head axle 350 and the collimator support 325, and aligning the centre of gravity of the detector head 305 with the axis of rotation of the detector head 305, which passes through the arm axles 340.

Once the locks 355 are in place, the detector head 305 will be balanced, and the detector head 305 can be rotated manually by the operator. Once the detector head 305 has been rotated to the desired position relative to the support arms 100, a brake (not shown) can be implemented to selectively prevent rotation of the detector head link about the arm axle 340.

Numerous modifications, variations and adaptations may be made to the particular embodiments of the invention described above without departing from the scope of the invention, which is defined in the claims.

I claim:

1. A positioner for a scintillation camera detector head, the detector head having a centre of gravity dependent upon the weight of a removable collimator plate and being supported by at least one support arm such that the detector head is rotatable relative to the support arm about an axis of rotation passing through the support arm, the positioner comprising:
   (a) a rigid detector head link comprising:
      (i) an arm end rotatably attached to the support arm by way of an arm axle defining a first axis of rotation for adjusting the angle of the detector head relative to the support arm; and
      (ii) head end rotatably attached to the detector head by way of a head axle defining a second axis of rotation for positioning the centre of gravity of the detector head relative to the first axis of rotation; and
   (b) a lock for selectively securing the relative positions of the detector head and the detector head link.

2. A positioner for a scintillation camera detector head, the detector head having a centre of gravity dependent upon the weight of a removable collimator plate and being supported between a pair of substantially parallel adjacent support arms such that the detector head is rotatable relative to the support arms about an axis of rotation passing through the support arms, the positioner comprising:
   (a) a pair of rigid detector head links for aligning the centre of gravity of the detector head relative to the support arms, each detector head link comprising:
      (i) an arm end rotatably attached to the adjacent support arm by way of an arm axle defining a first axis of rotation for adjusting the angle of the detector head relative to the support arm; and
      (ii) a head end rotatably attached to the detector head by way of a head axle defining a second axis of rotation for positioning the centre of gravity of the detector head relative to the first axis of rotation; and
   (b) a lock for selectively securing the relative positions of the detector head and the detector head links.

3. A positioner as defined in claim 2, wherein each rigid link is elongate and is substantially parallel to an adjacent support arm.

4. A positioner as defined in claim 2, comprising a pair of locks for selectively preventing rotation of the detector head relative to the detector head links.

5. A positioner as defined in claim 2, the lock comprising:
   (a) a collimator support extending from the detector head adjacent the collimator plate; and
   (b) a block for supporting the detector head link on the collimator support.

6. A positioner as defined in claim 5, each block comprising a pair of pins located either side of the head axle.

7. A positioner for a scintillation camera detector head, the detector head having a centre of gravity dependent upon the weight of a removable collimator plate and being supported between a pair of substantially parallel support arms such that the detector head is rotatable relative to the support arms about an axis of rotation passing through the support arms, the positioner comprising:
   (a) a pair of rigid elongated detector head links for aligning the centre of gravity of the detector head relative to the support arms, each detector head link being substantially parallel to an adjacent support arm and comprising;
      (i) an arm end rotatably attached to the adjacent support arm by way of an arm axle; and
      (ii) a head end rotatably attached to the detector head by way of a head axle; and
   (b) a pair of locks for selectively preventing rotation of the detector head relative to the detector head links, each lock comprising;
      (i) a collimator support extending from the detector head adjacent the collimator plate; and
      (ii) a block for supporting the detector head link on the collimator support, each block adapted to receive a pair of removable fixed length pins located either side of the head axle, wherein the pins installed are exchangeable with pins of a different length dependent on the weight of the collimator plate installed.

* * * * *